United States Patent [19]

Ackerman

[11] Patent Number: Plant 7,436

[45] Date of Patent: Feb. 5, 1991

[54] RASPBERRY PLANT NAMED PSI 79

[75] Inventor: Stephen M. Ackerman, Salinas, Calif.

[73] Assignee: Plant Sciences, Inc., Watsonville, Calif.

[21] Appl. No.: 398,432

[22] Filed: Aug. 25, 1989

[51] Int. Cl.[5] ..... A01H 5/00

[52] U.S. Cl. ..... Plt./46

[58] Field of Search ..... Plt. 46

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A raspberry plant named PSI 79, characterized by its everbearing fruit habit, high yield, early fruiting habit on second year floricanes, exceptional vigor, and reduced thorns.

3 Drawing Sheets

1

My invention relates to a new and distinct everbearing red raspberry variety named PSI 79 botanically known as *Rubus idaeus.* It was discovered by me as a chance seedling in a breeding plot established in 1987 on a ranch in Watsonville, Calif., provided by Well Pict, Inc. of Watsonville.

A breeding program was initiated jointly by Plant Sciences, Inc. and Coast Cooling, Inc., with the goal of developing new and distinct raspberry varieties. In 1987, my new variety was selected and extensively tested over the next year.

On Dec. 30, 1987, 15 to 20 dormant sucker canes of the variety were dug from the 1987 seedling field located on the Flats Ranch, Watsonville, Calif. All canes were hand dug as dormant root stock, cleaned, bagged and boxed. The canes were stored at a local cold storage facility at 28° F., until planting. These canes were planted on Jan. 26, 1988 in 15 to 20 linear feet of bed in the 1988 selection field, also located on the Flats ranch.

On Nov 30, 1988, 100 dormant sucker canes of the variety were dug from the 1988 selection field located on the Flats ranch, for further propagation. The following lists the planting dates, number of plants propagated and location of each planting.

| Planting Date | No. Plants | Location/Watsonville, CA |
|---|---|---|
| 12-30-88 | 40* | Peckham Ranch |
| 1-19-89 | 15** | Flats Ranch |
| 1-19-89 | 6* | Nakano Ranch |
| 1-25-89 | 20* | Peckham Ranch |
| 4-30/5-2-89 | 2,000–3,000*** | Flats Ranch |

*Planted as dormant bare root stock for field evaluations.

**Planted as dormant bare root stock for field evaluations in the 1989 advanced selection field.

***Planted for commercial nursery stock as greenhouse matured shoot tips propagated from 8–10 lbs. of roots.

* Planted as dormant bare root stock for field evaluations.  Planted as dormant bare root stock for field evaluations in the 1989 advanced selection field. * Planted for commercial nursery stock as greenhouse matured shoot tips propagated from 8–10 lbs. of roots.

The variety has been reproduced through asexually propagated sucker plants from selection fields in Watsonville, Calif. These daughter plants were then relocated for further testing on local grower fields associated with Well-Pict, Inc. in the Watsonville/Salinas area. Through these further tests and subsequent generations, the characteristics of this novel variety have remained fixed and true to type.

2

The following features are particularly outstanding in my new variety:

1. Everbearing fruiting habit, fruits on first year primocanes.
2. High yields, producing 30 percent of its overall spring production in July and 24 percent of its overall fall production in November.
3. Early fruiting habits on second year floricanes, typically one week earlier than Willamette and one week later than PSI 114 or PSI 127.
4. Exceptional vigor, producing twice as many suckers as Heritage.
5. Reduced thorns, about 50 percent smaller than Heritage.
6. About 30 percent taller than PSI 114, PSI 127 or PSI 168.
7. About 40 percent more fruiting laterals and 20 percent longer laterals than PSI 127 and PSI 114.
8. Very strong downward cupping of mature leaves.

The accompanying photographs show typical specimens of my new red raspberry variety at various stages of growth.

Photograph 1 shows a section of a typical primocane with its many small and reduced thorns. foliage, fruit, flowers, and a typical fruiting terminal.

Photograph 2 shows the development stages of a berry from flower to maturity, with the purple coloration of a typical primocane.

Photograph 3 depicts a typical fruiting terminal showing the fruit slightly protected under the foliage canopy, making this variety a little more difficult to pick. This photograph also shows the irregular shapes of the drupelets leading to irregularity of fruit shape.

FIG. 1 illustrates the electrophoresis patterns unique to this variety, as explained in detail below.

Production on first year primocanes begins approximately on July 1, yielding 1 percent of total production in July, 4 percent in August, 30 percent in September, 40 percent in October, and 24 percent in November, peaking during the middle of October. Berry size averages 3.0 to 3.2 grams from July through November, (about 15 percent larger than Heritage).

Spring production on second year floricanes begins approximately on May 7, yielding 20 percent of total production in May, 50 percent in June, and 30 percent in July, peaking during the middle of June. Berry size averages 2.3 to 2.5 grams from May through July, (about 20 percent smaller than Willamette).

The spring crop typically comprises 70 percent of the total production, with the fall crop comprising 30 percent. The spring crop precedes Willamette by approximately one week, with yields throughout the year exceeding those of both Heritage and Willamette.

The following is a detailed description of my new variety, PSI 79, based upon observations taken in Watsonville, Calif. Color terminology is in accordance with the Munsell Book of Colors, Munsell Color, Baltimore, Md. (1976).

Parentage: An open pollinated seedling of unknown parentage.

Fruit: Conditions when described; late (Oct. 27, 1988).

*Color.*—Red, color, 7.5R 3/8 to 7.5R 3/10.

*Size.*—Averages 18.7 mm long×18.5 mm wide (2.5 grams).

*Shape.*—Ovate, tapering to a rounded tip.

*Cavity.*—Funnel shaped, size averages 16.0 mm deep×8.0 mm wide.

*Receptacles.*—Cone shaped, size average 14.5 mm long×10.3 mm wide at the base, tapering to a sharp point. Color 10Y 9/4 to 10Y 8.5/4.

*Drupelets.*—Small, irregular in shape, average 70–80 per berry, and 15–16 around the outer rim.

*Seed.*—Small, average 2.8 mm long×1.6 mm wide×1.1 mm thick. Average weight, 1.4 milligrams per seed. Surface rugose. Color tan, 10YR 8/4 to 10YR 7/4.

*Sepals.*—Acuminate, number — 5, occasionally 6, color 5GY 6/6 to 5GY 7/6.

*Petals.*—Obovate, number — 5, occasionally 6.

*Quality.*—Very good fresh. Holds uniformity in color and appearance through cold storage and shipping. Fruit is slightly concealed under the canopy of the foliage, but detaches easily from the receptacle.

Plant: Data are an average of two evaluations, made on Sep. 23, 1988 and Oct. 12, 1988.

*Growth.*—Vigorous.

*Crown.*—Branched.

*Leaves.*—All samples were taken from a fully mature trifoliate, 10 to 12 trifoliates from the terminal bud. Leaves are typically smoothly rugose, with a strong downward cupping. Foliage is nearly always three foliate. Occasionally, the central leaflet will develop points to true independent leaflets, thus, creating a four foliate. Central leaflet: Size — averages 11.7 cm long×10.1 cm wide. Shape — cordate, tapering to an acuminate point. Color — upper surface, 7.5 GY 4/4 to 7.5 GY 3/4; lower surface, 5GY 7/2 to 5GY 6/2. Lateral leaflets: Size — averages 10.4 cm long×7.5 cm wide. Shape — ovate, tapering to an acuminate point. Petiole: averages 4.3 to 4.5 cm long and 3.0 to 3.2 mm in diameter.

*Canes.*—Moderately tall, average from 1.8 to 2.0 meters tall, with an average basal diameter of 1.4 to 1.6 cm. Color, evaluated on Feb. 10, 1989, is light — medium brown, 7.5YR 4/4 to 7.5YR 6/4. Internode length averages 4.0 to b 4.2 cm at mid cane. The plant produces on the upper 30 percent of its cane an average of 13 to 14 fruiting laterals, with an average length of up to 50–55 cm. Fruit is borne in raceme clusters averaging 13 to 14 berries per terminal prior to the first trifoliate.

*Suckers.*—Plant produces an average of 7–9 suckers per linear foot of bed planted in a single row and spaced 12 inches apart. Average basal diameter — 0.7 to 0.9 cm. Glabrous, with many small strout prickles, heavy at the base, averaging 40 per cm of cane by 2.0 mm long to 10 per cm at the tip by 0.9 mm long. Internode length averages 5.1 to 5.3 cm at mid cane. Color is light green, 5GY 7/4 to 5GY 6/4. With age and exposure to the sun, suckers tend toward a purple coloration, 10RP 3/6 to 10RP 5/6.

Studies of protein polymorphism in Rubus by the starch gel electrophoresis method were carried out to characterize this newly developed variety and distinguish it from other varieties.

Isozymes were extracted from y oung leaves and characterized using starch gel electrophoresis techniques. The following isozymes were characterized: malate dehydrogenase (MDH: EC 1.1.1.37); triose phosphate isomerase (TPI: EC 5.3.1.1); phosphoglucoisomerase (PGI: EC 5.3.19) and phosphoglucomutase (PGM: EC 2.7.5.1).

The The plant material used was both field and green-house in Watsonville, Calif. Newly matured leaves (1 g fresh weight) from the growing tips of canes were used. Samples were held at 4–8 C and analyzed within 24 hours of collection.

The tris extraction buffer (pH 8.0) was as follows: 0.05M tris base, 0.007M citric acid (monohydrate), 0.1% cysteine hydrochloride, 0.1% ascorbic acid (Na salt or free acid), 1.0% polyethylene glycol, and 80 ul/l 2-mercaptoethanol. Samples were extracted in 10–12 ml cold buffer by homogenizing at 17,000 rpm.

Gel and electrode buffers for enzyme systems analyzed are given in Table 1. Electrophoresis specifications for these enzyme systems are given in Table 2.

The starch gel was prepared and held overnight at 20C±5C prior to use. To form the starch gel, potato starch (30 g) is dissolved in 80 ml of cold gel buffer (System A: gel buffer 50 ml/electrode buffer 30 ml) in a vacuum flask (1.0 l). Boiling gel buffer (220 ml) is added to the starch solution. Starch is completely dissolved by vigorously swirling the solution in the vacuum flask, and vacuumed for 15 to 30 seconds. Gel solution is immediately poured onto a 20.5×22.0 cm plexiglass gel plate and covered until use.

Samples are inoculted onto paper wicks and placed in a cooled gel (4C); covered with Saran and electrophoresed for 20 minutes. The wicks are removed and the system is run until the dye front travels approximately 5–8 cm.

Following electrophoresis, the gel is sliced into four equal slices and stained for each enzyme system. Banding patterns are interpreted as they develop and gel slices are fixed in 50% glycerol.

TABLE 1

| SYSTEM | pH | GEL BUFFER | G/L | ELECTRODE BUFFER | G/L | pH |
|---|---|---|---|---|---|---|
| A | 8.3 | Tris Base | 65 | Lithium Hydroxide | 1.2 | 8.3 |
| | | Citric Acid (Monoh) | 1.5 | Boric Acid | 12.0 | |
| B | 7.0 | DL-Histidine HCL (Monohydrate) | 1.2 | Tris Base | 16.5 | 7.0 |
| | | | | Citric Acid (Monohyd.) | 9.0 | |
| C | 7.8 | Tris Ultra Pure | 1.09 | Tris Ultra Pure | 16.35 | 7.8 |

TABLE 1-continued

| SYS-TEM | pH | GEL BUF-FER | G/L | ELECTRODE BUFFER | G/L | pH |
|---|---|---|---|---|---|---|
| | | Citric Acid | 0.63 | Citric Acid | 9.03 | |
| | | $Na_2EDTA$ | 0.45 | $Na_2EDTA$ | 0.45 | |

TABLE 2

RUBUS ELECTROPHORESIS SPECIFICATIONS

| SYSTEM | ENZYME | pH | CURRENT | GEL SLICE # |
|---|---|---|---|---|
| A | PGI | 8.3 | 275V | 2 |
| A | LAP | 8.3 | 275V | 4 |
| B | MDH | 7.0 | 150V | 2 |
| B | PGM | 7.0 | 150V | 3 |

TABLE 2-continued

RUBUS ELECTROPHORESIS SPECIFICATIONS

| SYSTEM | ENZYME | pH | CURRENT | GEL SLICE # |
|---|---|---|---|---|
| C | TPI | 7.8 | 50mA | 2 |

The isozyme banding patterns for the four enzyme systems compared to those of Heritage are given in FIG. 1 The RF value is the ratio between the distance (cm) traveled by the band to the distance traveled by the dye front (cm).

My new variety may not be resistant to any known diseases and insects. It is known to be susceptible to powdery mildew and rust. This new variety may vary slightly in its characteristics, depending upon weather, soil, location, and evaluation dates.

What is claimed is:

1. A new distinct variety of red raspberry plant named PSI 79, as herein described and illustrated.

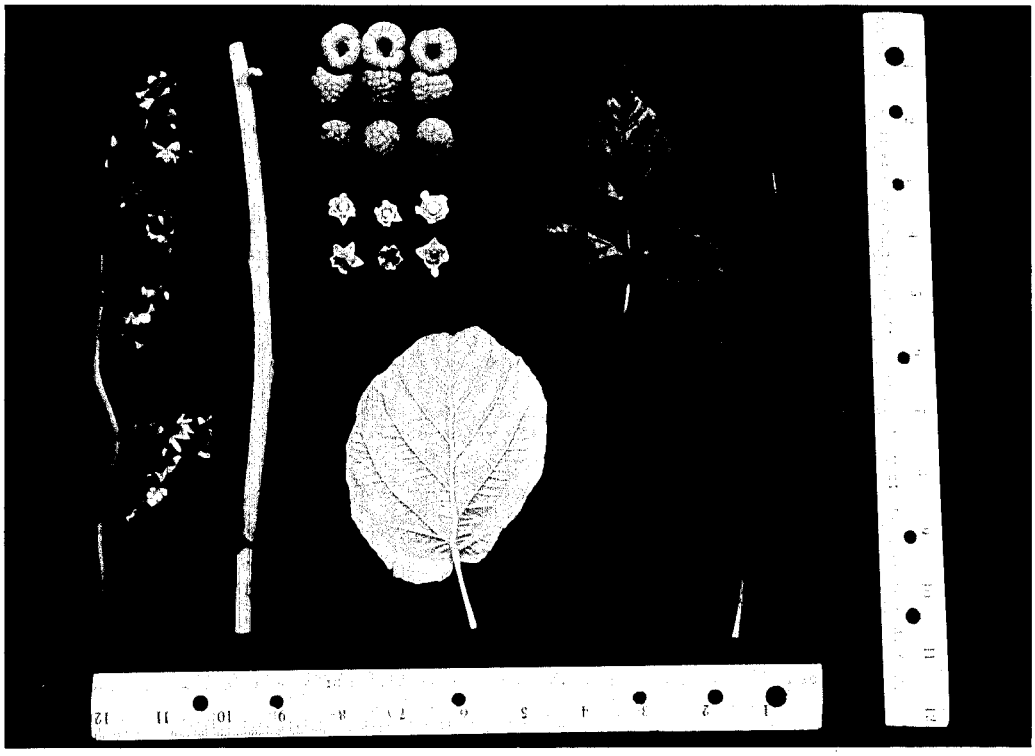

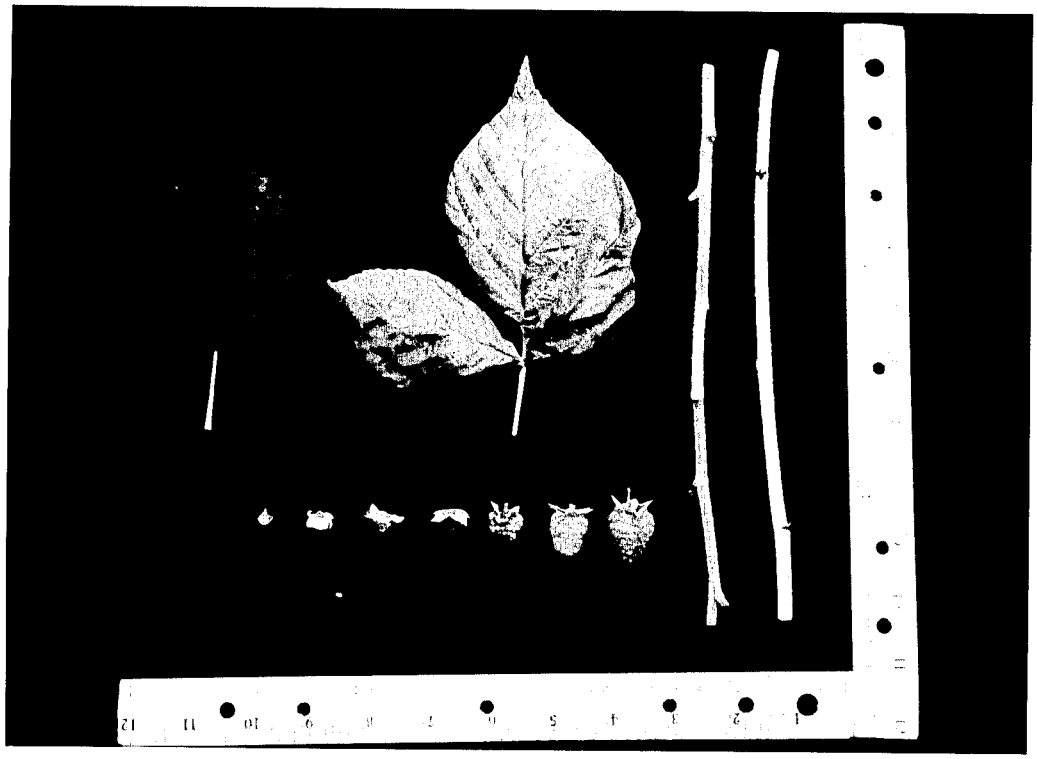

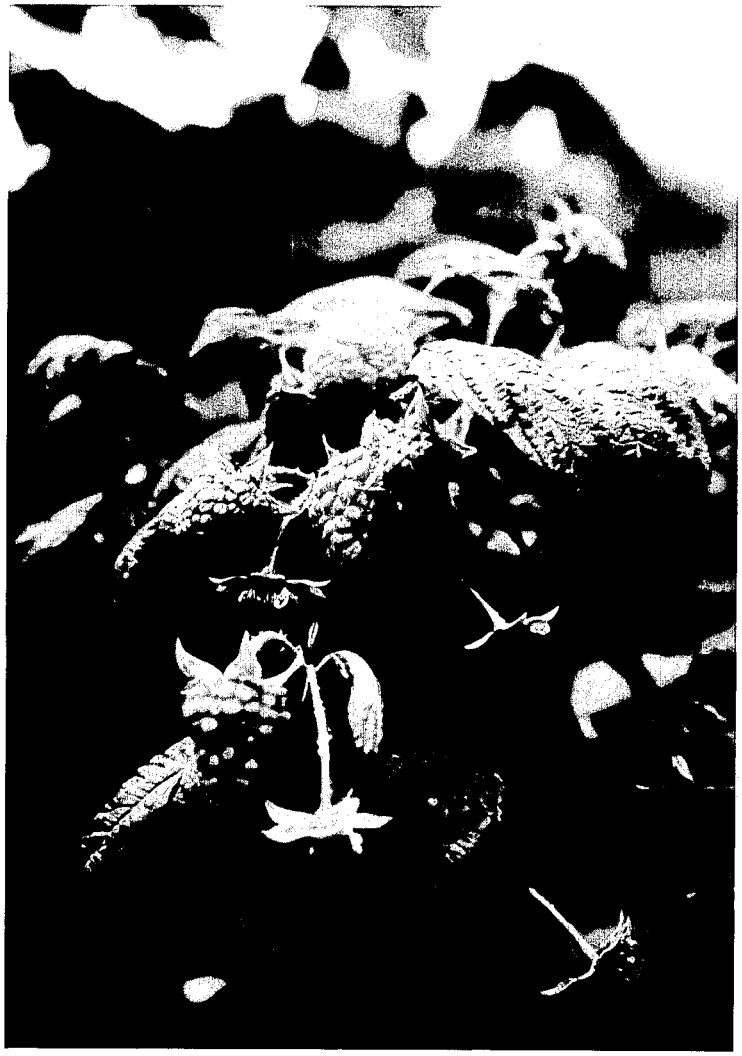

* * * * *